United States Patent
Kim

(10) Patent No.: US 6,857,874 B2
(45) Date of Patent: Feb. 22, 2005

(54) DENTAL IMPLANT STRUCTURE

(76) Inventor: Man Yong Kim, #603-103 Jungbangmaeul, 1006, Madu-dong, Ilsan-gu, 411-714 Goyang-si, Kyunggi-do (KR)

( * ) Notice: Subject to any disclaimer, the term of this patent is extended or adjusted under 35 U.S.C. 154(b) by 283 days.

(21) Appl. No.: 10/247,314

(22) Filed: Sep. 19, 2002

(65) Prior Publication Data

US 2003/0215769 A1 Nov. 20, 2003

(30) Foreign Application Priority Data

May 16, 2002 (KR) ........................................ 2002-27055

(51) Int. Cl.[7] ................................................ A61C 8/00
(52) U.S. Cl. ...................... 433/173; 433/172; 433/174
(58) Field of Search ................................ 433/172, 173, 433/174

(56) References Cited

U.S. PATENT DOCUMENTS 6,488,502 B1 * 12/2002 Weber ........................ 433/173

* cited by examiner

Primary Examiner—Cary E. O'Connor
Assistant Examiner—Candice C. Melson
(74) Attorney, Agent, or Firm—Bachman & LaPointe, P.C.

(57) ABSTRACT

Disclosed is a dental implant which is implanted into an edentulous site of the jawbone to function as a substitute for a lost tooth. The dental implant according to the present invention includes: a fixture having a screw coupling hole formed at the inside thereof along the central axis thereof by a predetermined depth, the fixture being opened at the upper end thereof, and a threaded screw part formed on the outer circumferential surface thereof; an abutment secured to the upper end of the fixture and having a locking slit formed at the upper portion of the outer circumferential surface thereof; a screw coupled to the screw coupling hole of the fixture through the abutment and having a sleeve inserting groove formed at the upper portion thereof to be connected to the locking slit of the abutment; and a locking sleeve fitted into both the locking slit of the abutment and the sleeve inserting groove of the screw.

5 Claims, 6 Drawing Sheets

DENTAL IMPLANT STRUCTURE

BACKGROUND OF THE INVENTION

1. Field of the Invention

The present invention relates to a dental implant, and more particularly, to a dental implant which is embedded into an edentulous site of the jawbone to function as a substitute for a lost tooth.

2. Background of the Related Art

A study on methods for finding a substitute for a tooth that is lost due to various reasons has been continued in dentistry. Clinical testing for finding the methods has been actively conducted as well. Among the methods, the most widely used method is to use a crown or a bridge as an artificial substitute for the lost tooth with the help of adjacent teeth, or to use a partial denture or a complete denture as the artificial substitute for the lost tooth with the help of both the adjacent teeth and gums(jawbone).

The above crown or bridge is disadvantageous in that the adjacent healthy teeth should be pulled out, and if there are lots of lost teeth, the crown or bridge has a limitation in functioning as the artificial substitute for the lost teeth and bearing occlusive pressure. Additionally, it is said to be inconvenient to use and store.

There has recently been great technical development in dentistry. The modern technology has finally developed an artificial tooth, namely implant, made of titanium that is biocompatible and thus doesn't cause any physiologic disorder even though it is attached to a human body for a long period of time.

Most conventional dental implants, as shown in FIG. 1, include a fixture 2 having a screw part 1, and an abutment 3 integrally formed with the upper end of the fixture, such that the fixture 2 and the abutment 3 are fixedly secured to each other by means of a screw 4.

The dental implant 10 constructed as above couples the fixture 2 and the abutment 3 by means of the general screw 4, whereby during an external impact, the screw 4 often comes loose and the screw 4 may be damaged due to a serious impact.

Furthermore, the connection between the fixture and the abutment by the screw should be checked periodically, which is very inconvenient and annoying for a patient as well as a dentist. Moreover, a considerable amount of cost for checking the connection is incurred.

SUMMARY OF THE INVENTION

Accordingly, the present invention is directed to a dental implant that substantially obviates one or more problems due to limitations and disadvantages of the related art.

An object of the present invention is to provide a dental implant capable of fundamentally preventing a screw-loosening problem.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a dental implant comprising: a fixture having a screw coupling hole formed at the inside thereof along the central axis thereof by a predetermined depth, the fixture being opened at the upper end thereof, and a threaded screw part formed on the outer circumferential surface thereof; an abutment secured to the upper end of the fixture and having a locking slit formed at the upper portion of the outer circumferential surface thereof; a screw coupled with the screw coupling hole of the fixture through the abutment and having a sleeve inserting groove formed at the upper portion thereof to be connected to the locking slit of the abutment; and a locking sleeve fitted into both the locking slit of the abutment and the sleeve inserting groove of the screw.

It is to be understood that both the foregoing general description and the following detailed description of the present invention are exemplary and explanatory and are intended to provide further explanation of the invention as claimed.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will now be made in detail to the preferred embodiments of the present invention, examples of which are illustrated in the accompanying drawings.

Figure 1:
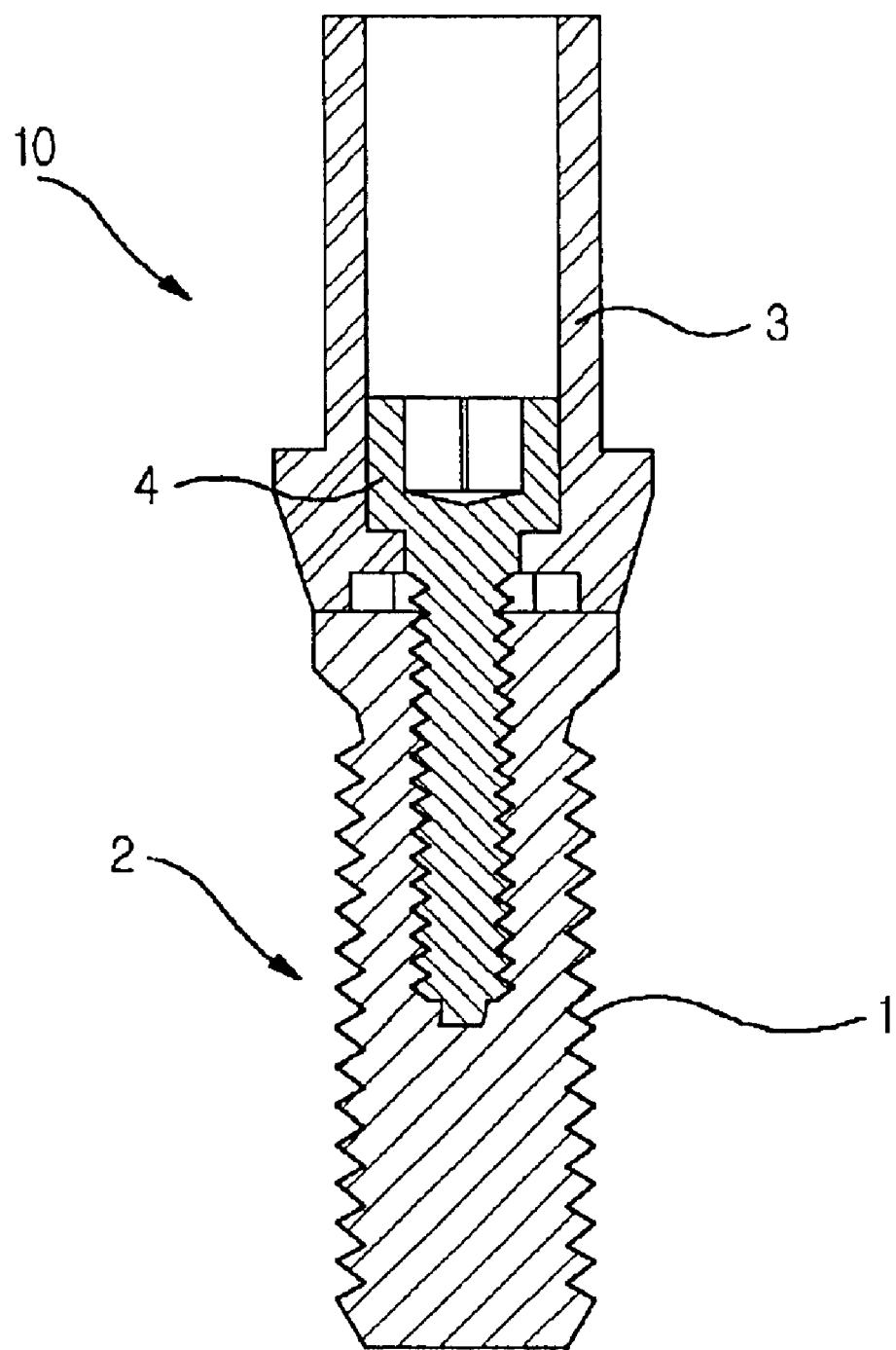
FIG. 1 is a cross-sectional view of a conventional dental implant.
Figure 2:
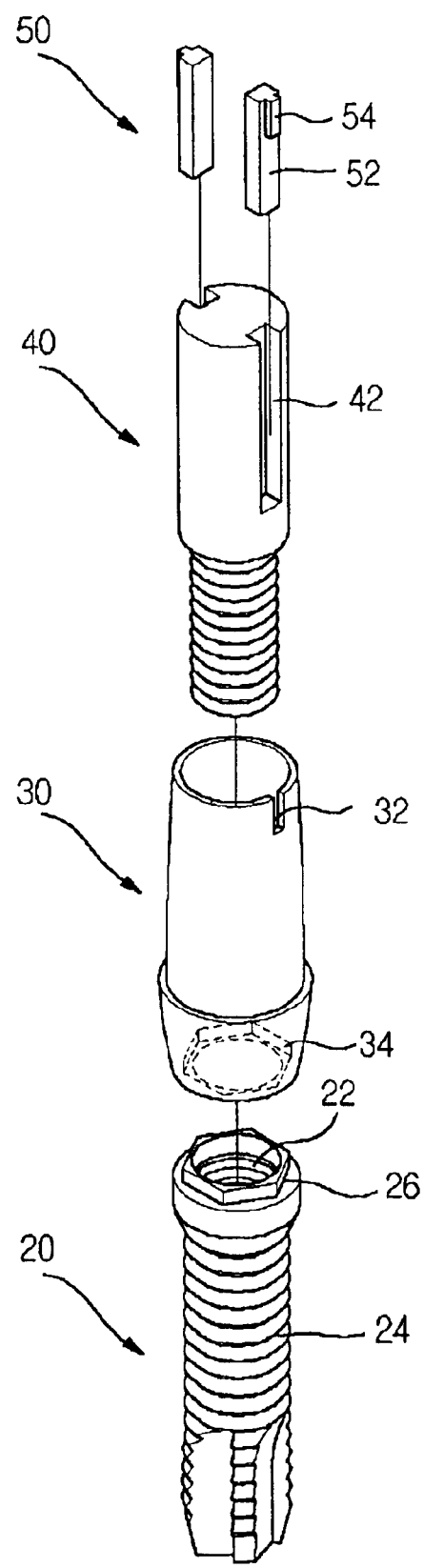
FIG. 2 is an exploded perspective view of a dental implant according to the present invention.
Figure 3:
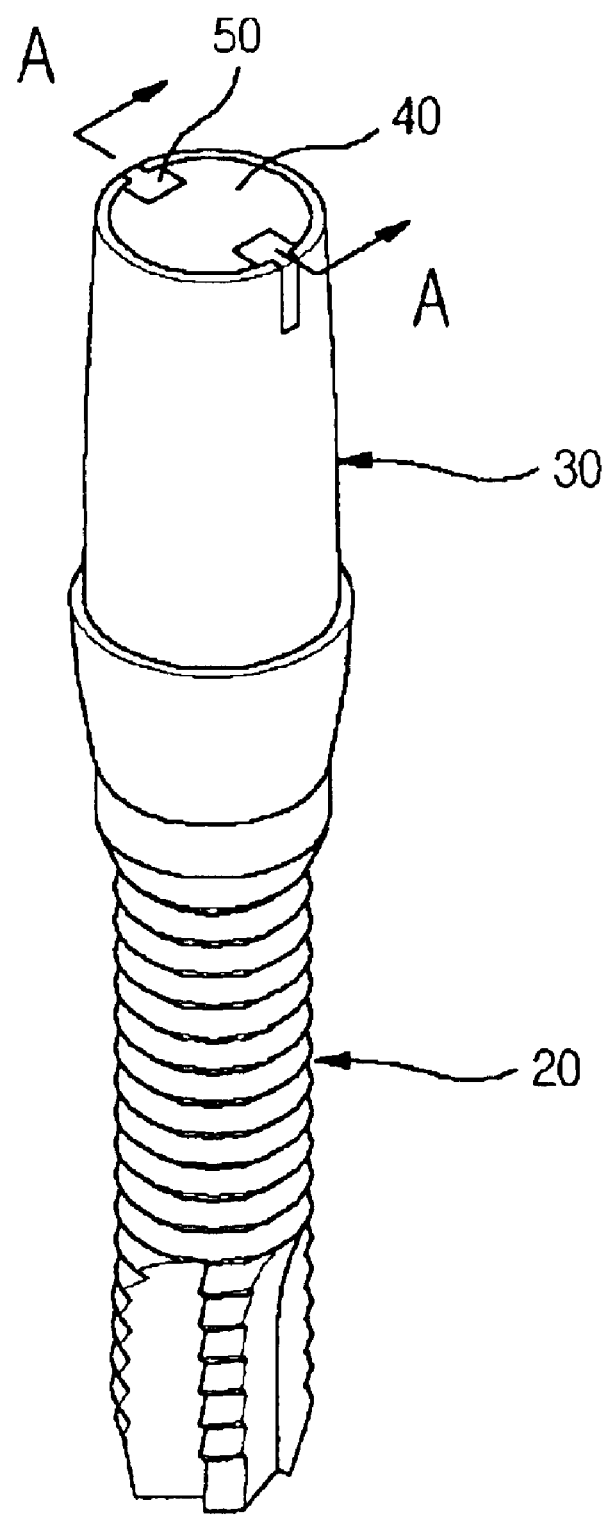
FIG. 3 is a perspective view of the assembled dental implant of FIG. 2 according to the present invention.
Figure 4:
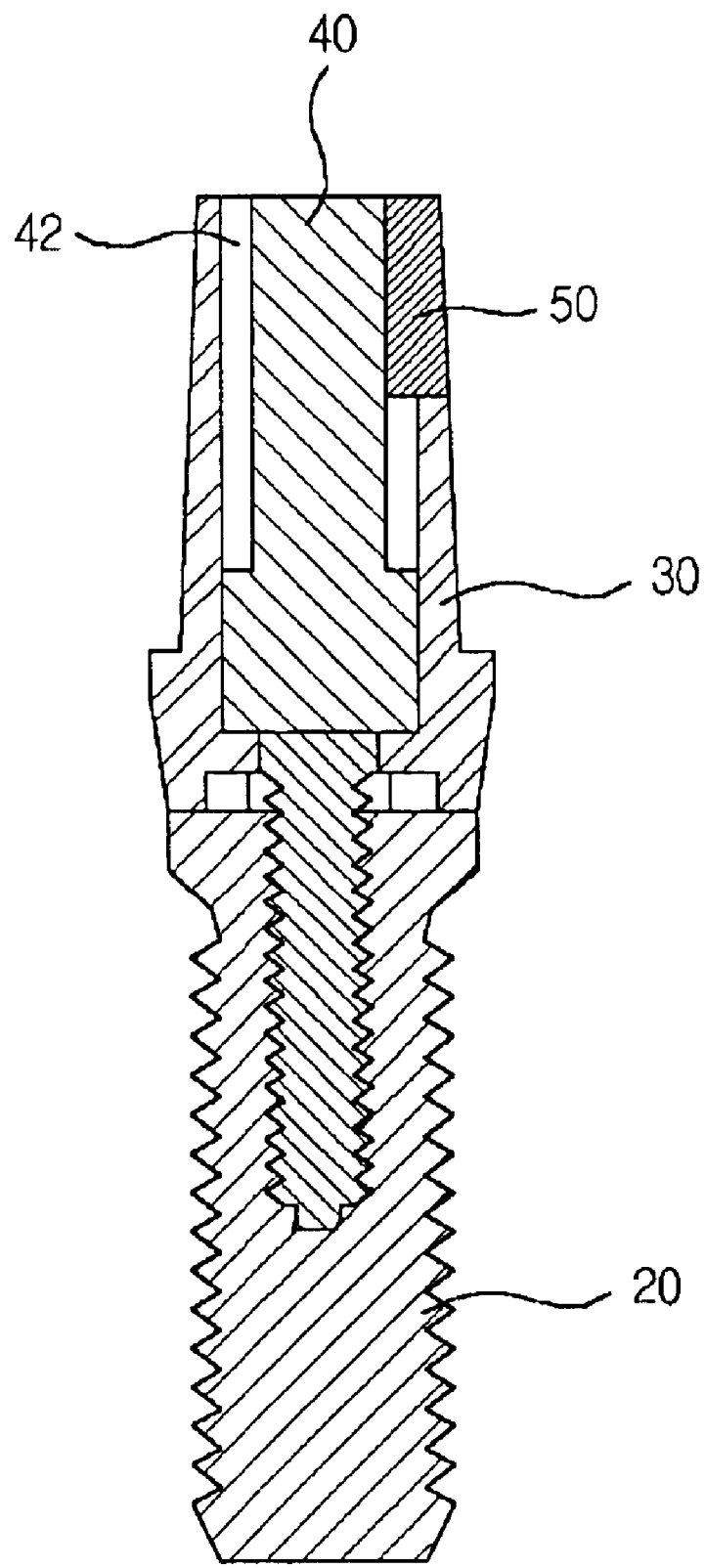
FIG. 4 is a cross-sectional view taken along the line A—A of FIG. 3 according to the present invention.

FIG. 2 is an exploded perspective view of a dental implant according to the present invention, FIG. 3 is a perspective view of the assembled dental implant of FIG. 2 according to the present invention, and FIG. 4 is a cross-sectional view taken along the line A—A of FIG. 3 according to the present invention.

Referring to FIGS. 2 to 4, a dental implant includes: a fixture 20 having a screw coupling hole 22 formed at the inside thereof along the central axis thereof by a predetermined depth, the fixture being opened at the upper end thereof, and a threaded screw part 24 formed on the outer circumferential surface thereof; an abutment 30 secured to the upper end of the fixture 20 and having a locking slit 32 formed at the upper portion of the outer circumferential surface thereof; a screw 40 coupled to the screw coupling hole 22 of the fixture 20 through the abutment 30 and having a sleeve inserting groove 42 formed at the upper portion thereof to be connected to the locking slit 32 of the abutment 30; and a locking sleeve 50 fitted into both the locking slit 32 of the abutment 30 and the sleeve inserting groove 42 of the screw 40.

A coupling part 26 of hexagonal shape is formed at the upper end of the fixture 20 and a corresponding recess part 34 is formed at the lower end of the abutment 30, such that the coupling part 26 and the recess part 34 are coupled to each other, thereby preventing rotation of the screw. The coupling part 26 and the recess part 34 are not restricted to the hexagonal shape but can be manufactured to have various shapes.

The abutment 30 is in a taper shape and maintains a sealing state with the fixture 20 to prevent any foreign substances from entering thereinto.

The screw 40 functions to fixedly connect the fixture 20 and the abutment 30, and has a helical portion formed at the lower side thereof such that the helical portion is coupled with the screw coupling hole 22 of the fixture 20. The sleeve inserting groove 42 of the screw 40 is formed in at least twos in order to be easily rotated, that is, to be coupled or separated by means of a working tool.

In the meanwhile, the locking sleeve 50 serves to prevent the screw 40 from loosening, and includes a body 52 which is inserted into the sleeve inserting groove 42 of the screw 40 and a projection 54 which is integrally formed with the body 52 and supportably seated in the locking slit of the abutment 30.

Figure 5:
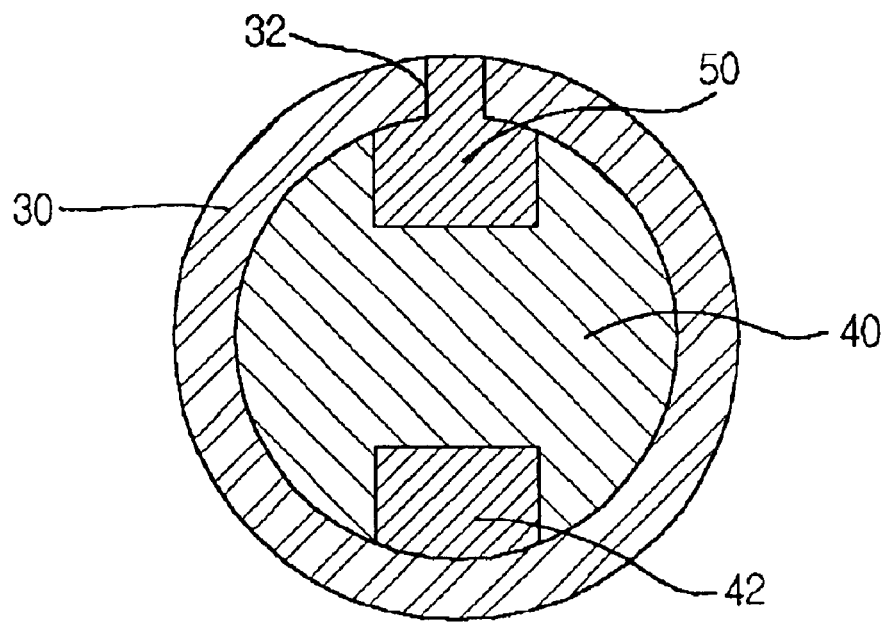
FIG. 5 is a cross-sectional view of a dental implant viewed from above according to a first preferred embodiment of the present invention, in which an abutment, a screw and a locking sleeve of the dental implant are coupled with one another.
Figure 6:
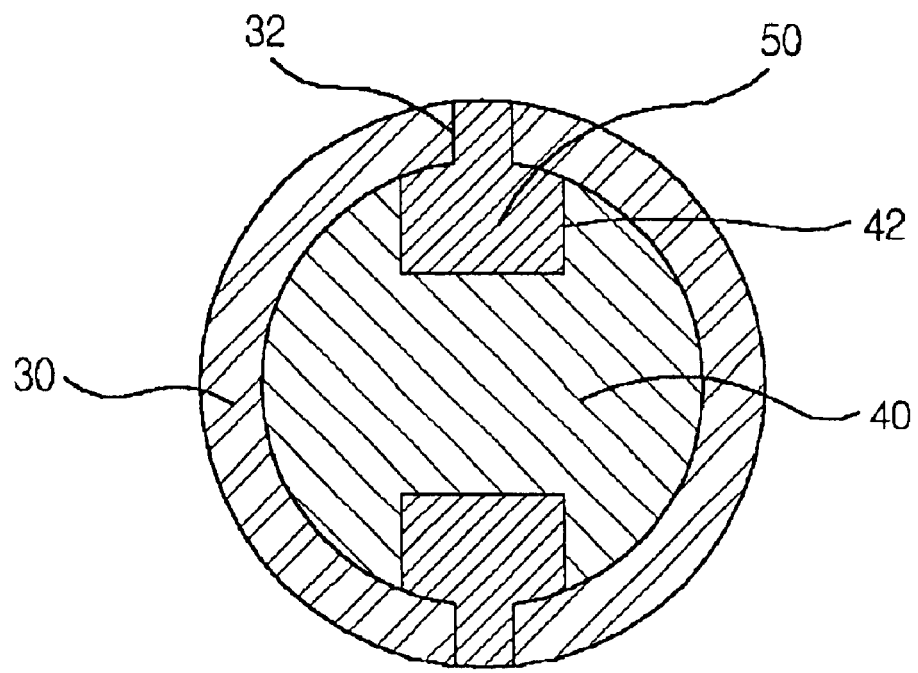
FIG. 6 is a cross-sectional view of a dental implant viewed from above according to a second preferred embodiment of the present invention.
Figure 7:
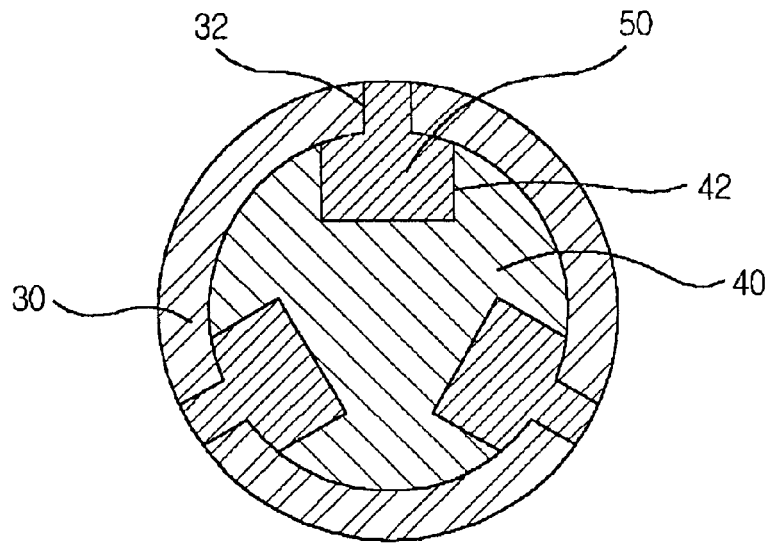
FIG. 7 is a cross-sectional view of a dental implant viewed from above according to a third preferred embodiment of the present invention.

FIG. 5 is a cross-sectional view of a dental implant viewed from above according to a first preferred embodiment of the present invention, illustrating a state in which an abutment, a screw and a locking sleeve are coupled with another, FIG. 6 is a cross-sectional view of a dental implant viewed from above according to a second preferred embodiment of the present invention, and FIG. 7 is a cross-sectional view of a dental implant viewed from above according to a third preferred embodiment of the present invention.

Referring to FIGS. 5 to 7, the sleeve inserting groove 42 of the screw 40 is formed in twos, as shown in FIG. 5, and the locking slit 32 of the abutment 30 is optionally formed on either of the sleeve inserting grooves 42, so that the locking sleeves 50 can be fitted into the sleeve inserting grooves 42 of the screw 40 and the locking slit 32 of the abutment 30. As illustrated in FIGS. 6 and 7, the sleeve inserting groove 42 of the screw 40 and the locking slit 32 of the abutment 30 are formed in twos or threes, such that the locking sleeves 50 are respectively fitted into the sleeve inserting grooves 42 of the screw 40 and the locking slits 32 of the abutment 30, thereby achieving tighter connection between the screw and the abutment.

The sleeve inserting grooves 42 of the screw 40 can be formed in other plural numbers at needs, but the size of the implant is so small that to form relatively larger number of sleeve inserting grooves 42 has a limitation in structure. Two or three sleeve inserting grooves are most preferably used.

Figure 8:
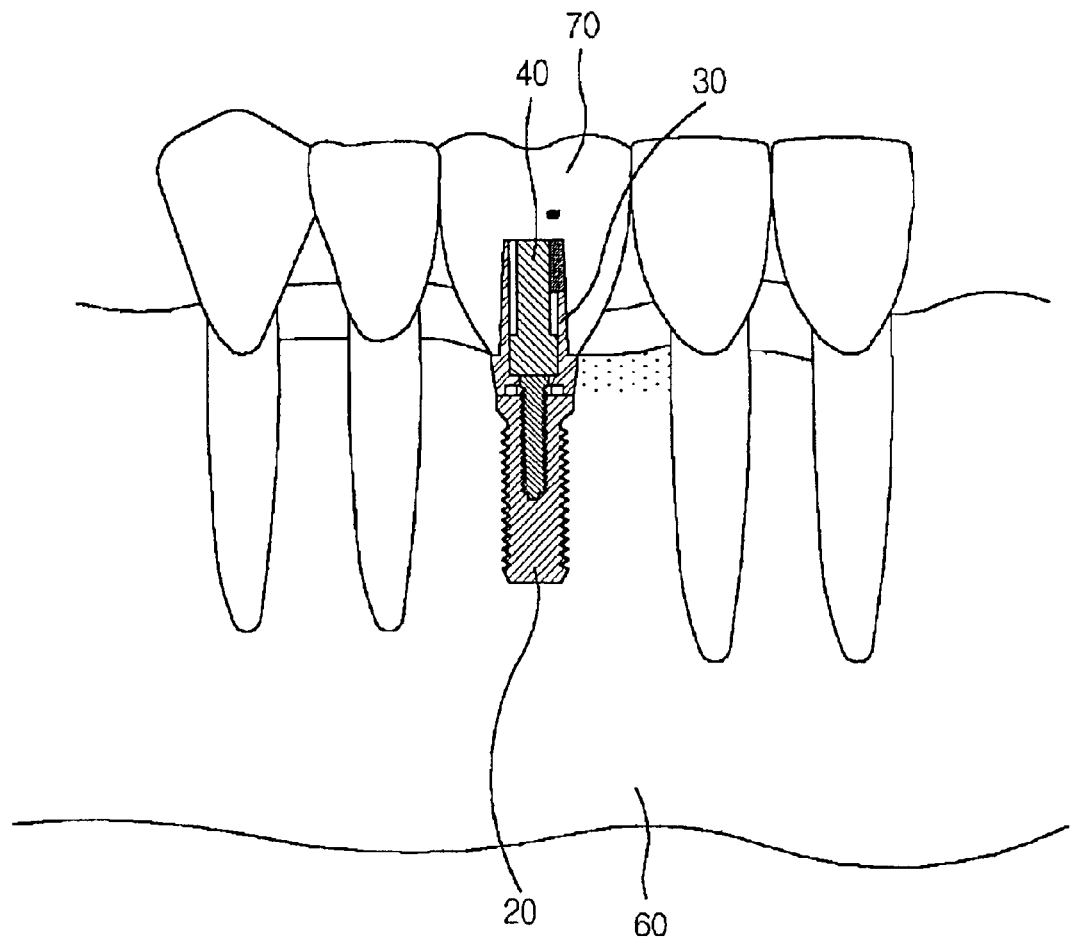
FIG. 8 is a schematic view illustrating a state in which the dental implant is applied to the teeth according to the present invention.

FIG. 8 is a schematic view illustrating a state in which the dental implant is applied to the teeth according to the present invention. The clinical application is roughly performed through three steps according to the nature of work and will be described in brief hereinbelow:

(a) implanting the fixture 20 into an edentulous site of a jawbone 60 and waiting until the fixture 20 is firmly coupled, wherein if the jawbone is in the upper jaw, 6 months or so are required, whereas if it is in the lower jaw, 4 months or so are required;

(b) connecting the abutment 30 to the upper end of the fixture 20 and tightly fix them together by means of the screw 40; and (c) placing a final prosthesis, such as a crown, a denture, etc., over the abutment 30, finishing the operation.

The aforesaid steps are commonly performed in the dental implant operation.

As described above, the present invention applies the locking sleeve to the dental implant so as to fundamentally prevent the screw loosening which often occurs in the conventional art.

Accordingly, efficiency in the dental operation is enhanced and a patient's inconvenience is solved. Besides, the present invention is advantageous in an economic aspect since additional maintenance costs are reduced.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A dental implant comprising:
    a fixture having a screw coupling hole formed at the inside thereof along the central axis thereof by a predetermined depth, the fixture being opened at the upper end, and a threaded screw part formed on the outer circumferential surface thereof;
    an abutment secured to the upper end of the fixture and having a locking slit formed at the upper portion of the outer circumferential surface thereof;
    a screw coupled to the screw coupling hole of the fixture through the abutment and having a sleeve inserting groove formed at the upper portion thereof to be connected to the locking slit of the abutment; and
    a locking sleeve fitted into both the locking slit of the abutment and the sleeve inserting groove of the screw.

2. The dental implant as claimed in claim 1, wherein the locking sleeve includes a body inserted into the sleeve inserting groove of the screw, and a projection integrally formed with the body and supportably seated in the locking slit of the abutment.

3. The dental implant as claimed in claim 1, wherein the sleeve inserting groove of the screw is formed in two or three, and the locking slit of the abutment is formed to be optionally connected to one of the sleeve inserting grooves.

4. The dental implant as claimed in claim 1, wherein the sleeve inserting groove of the screw and the locking slit of the abutment are formed in two, respectively.

5. The dental implant as claimed in claim 1, wherein the sleeve inserting groove of the screw and the locking slit of the abutment are formed in three, respectively.

\* \* \* \* \*